US008039262B2

(12) United States Patent
Konrad et al.

(10) Patent No.: US 8,039,262 B2
(45) Date of Patent: Oct. 18, 2011

(54) METHOD FOR CONTROLLING A TISSUE PROCESSOR AND TISSUE PROCESSOR

(75) Inventors: Marc Konrad, Dossenheim (DE); Holger Metzner, Hassloch (DE); Udo Hermann, Leimen (DE); Frank Meder, Bammental (DE); Hermann Ulbrich, Bad Schönborn-Mingolsheim (DE); Markus Dobusch, Wiesloch-Baiertal (DE); Stefan Künkel, Karlsruhe (DE)

(73) Assignee: Leica Biosystems Nussloch GmbH, Nussloch, DE (US)

( * ) Notice: Subject to any disclaimer, the term of this patent is extended or adjusted under 35 U.S.C. 154(b) by 214 days.

(21) Appl. No.: 12/545,586

(22) Filed: Aug. 21, 2009

(65) Prior Publication Data
US 2010/0055663 A1 Mar. 4, 2010

(30) Foreign Application Priority Data
Aug. 27, 2008 (DE) .......................... 10 2008 039 876

(51) Int. Cl.
*C12Q 3/00* (2006.01)
*C12M 1/36* (2006.01)
*C12M 3/00* (2006.01)
*G01N 33/48* (2006.01)

(52) U.S. Cl. ................. 436/55; 436/43; 436/50; 436/63; 422/67; 435/3; 435/40.5; 435/40.52; 435/283.1; 435/286.1

(58) Field of Classification Search .................... 436/43, 436/50, 55, 63, 149; 422/67, 68.1; 435/3, 435/40.5, 40.52, 283.1, 286.1
See application file for complete search history.

(56) References Cited

U.S. PATENT DOCUMENTS

| 5,560,956 | A | 10/1996 | Schmehl |
| 6,465,245 | B1 | 10/2002 | Walton et al. |
| 6,780,380 | B2 * | 8/2004 | Hunnell et al. ............... 422/536 |
| 6,793,890 | B2 * | 9/2004 | Morales et al. ............... 422/536 |
| 7,235,140 | B1 | 6/2007 | Hayes et al. |
| 7,722,811 | B2 * | 5/2010 | Konrad et al. .................. 422/63 |
| 2007/0243626 | A1 | 10/2007 | Windeyer et al. |
| 2008/0153158 | A1 * | 6/2008 | Drummond ..................... 435/325 |
| 2008/0220468 | A1 * | 9/2008 | Windeyer et al. .......... 435/40.52 |
| 2009/0298172 | A1 * | 12/2009 | Wheeler ....................... 435/374 |
| 2010/0055777 | A1 * | 3/2010 | Rapp et al. ................. 435/309.1 |

FOREIGN PATENT DOCUMENTS

| DE | 215767 | 11/1909 |
| DE | 10128126 | 12/2002 |

* cited by examiner

*Primary Examiner* — Maureen Wallenhorst
(74) *Attorney, Agent, or Firm* — Schlee IP International, P.C.; Alexander R. Schlee

(57) ABSTRACT

A method for controlling a tissue processor and a tissue processor for processing tissue samples is described. A retort is provided including a cover that can be opened and closed by an operator. The retort cover is closed prior to tissue processing. The actuation state of a first and a second operating element can be determined. An operator is prompted to confirm unlocking of the closed retort cover by actuating a second operating element. The tissue processing is interrupted when an actuation of the second operating element is determined and the closed retort cover is unlocked and is continued after the retort cover is once again locked. After having completed tissue processing the retort cover is unlocked. By means of the described method and tissue processor improper intervention during ongoing tissue processing is prevented.

16 Claims, 4 Drawing Sheets

METHOD FOR CONTROLLING A TISSUE PROCESSOR AND TISSUE PROCESSOR

CROSS-REFERENCE TO RELATED APPLICATION

This application claims the priority of the German patent application DE 102008039876.4 having a filing date of Aug. 27, 2008. The entire content of this prior German patent application DE 102008039876.4 is herewith incorporated by reference.

BACKGROUND OF THE INVENTION

The invention relates to a method for controlling a tissue processing having a retort in which a process for the treatment of tissue samples is carried out, and which has a retort cover to be opened and closed by an operator. The invention further relates to a tissue processor.

The assessment of cells and their environment requires biological tissue samples that are observed under a microscope. For microscopic inspection, thin sections of the tissue samples must be prepared, for example, by means of a microtome. In order to allow the tissue samples to be sectioned, they must first, in multiple process steps, be dewatered, cleaned, hardened, and then stabilized, for example, with paraffin. This is often accomplished in a single unit intended for this purpose, called a "tissue processor."

The tissue processor has a process chamber, also referred to as a "retort," in which the tissue samples are arranged and the treatment process is automatically carried out. The retort has a retort cover that an operator manually opens and closes in order to place the tissue samples into the retort and, once the treatment process has been carried out, remove them from the retort.

The tissue samples are treated in the retort with a variety of reagents. These reagents generate vapors to which the operator is exposed when the retort is opened. To avoid excessive impact on the operator as a result of such vapors, the tissue processor often comprises a ventilator apparatus. This communicates with the retort and discharges the vapors occurring in the retort, for example, through the back side of the tissue processor.

Reference is made in this connection, by way of example, to U.S. Pat. No. 6,465,245 B1, which describes a tissue processor having a ventilator apparatus that is continuously in operation or that is put into operation at least upon opening of the retort. Reference is also made to DE 101 28 126 A1, which describes a method for extracting toxic vapors during the fixing of tissue samples.

In conventional tissue processors, the retort cover can also be opened manually during the treatment process, for example in order to remove one of the tissue samples from the retort or to introduce a further tissue sample into the retort. The possibility of opening the retort cover during the treatment process entails, however, the risk of improper intervention in the process sequence, so that the quality of the treated tissue samples is not continuously ensured.

SUMMARY OF THE INVENTION

The object of the invention is to describe a method for controlling a tissue processor, and a tissue processor, that enable improper intervention in the ongoing treatment process to be avoided.

The tissue processor according to the present invention comprises a control device for controlling the tissue processor having a mechanism for locking and unlocking a closed retort cover, a first operating element that can be actuated by an operator, a second operating element that can be actuated by the operator, and a display apparatus. The tissue processor further comprises a retort in that the tissue is processed and that is connected to the retort cover to be opened and closed by an operator. The control device is adapted to perform the following method achieving the object of the invention by the method steps of locking the closed retort cover prior to tissue processing to prevent opening, determining the actuation state of a first operating element that can be actuated by the operator, prompting the operator when an actuation of the first operating element during tissue processing is determined by displaying to the operator on a display device the prompt to confirm unlocking of the closed retort cover by actuating a second operating element that can be actuated by the operator, determining the actuation state of the second operating element, interrupting tissue processing when an actuation of the second operating element is determined and the closed retort cover is unlocked, continuing tissue processing after the retort cover is once again locked, and unlocking the retort cover after having completed tissue processing.

According to the present invention, the retort cover, closed manually by the operator before the treatment process starts, is locked so that the retort cover can no longer be opened by the operator. During execution of the treatment process, the actuation state of a first operating element is monitored. If the operator wishes to open the retort cover during the treatment process, he or she actuates the first operating element. Actuation of the first operating element during the treatment process is sensed, whereupon the operator is prompted, on a display apparatus, to actuate a second operating element in order to confirm unlocking of the closed retort cover. Only when actuation of the second operating element is sensed does the method according to the present invention interrupt the treatment process and unlock the closed retort cover. The unlocked retort cover can now be opened manually by the operator. The treatment process is not continued until after the closed retort cover is once again locked. Once the treatment process is finally complete, the retort cover is unlocked again and the operator can take the treated tissue samples out of the retort.

In the method according to the present invention, the treatment process automatically carried out by the tissue processor is therefore interrupted, and the retort cover unlocked, when the operator first actuates the first operating element and then, after prompting, actuates the second operating element. Inadvertent opening of the retort during execution of the treatment process can thereby be avoided.

The control method offers, in particular, the possibility of interrupting the treatment process in defined fashion before the operator obtains access to the tissue samples. This defined interruption then also makes it possible to continue the treatment process in defined fashion once the retort cover has again been locked. The quality of the treated tissue samples is thereby continuously ensured.

The first and the second operating element can also be embodied as a single bifunctional operating element.

In an advantageous refinement, a ventilator apparatus connected to the retort is operated at a first power level during the execution of the treatment process, and at a second power level that is higher than the first power level during the interruption of the treatment process. If the retort cover is opened manually by the operator during the interruption of the treatment process, the ventilator apparatus that is operating at a higher power level in this case ensures that the vapors produced in the retort are extracted particularly effectively. The operator is thereby protected from these vapors upon opening of the retort.

If at least one of the method steps according to the present invention is recorded in a log file, it is possible to ascertain later, on the basis of the log file, the manner in which the treatment process proceeded. In particular, an interruption of the treatment process by the operator, which interruption might have effects on the quality of the treated tissue samples, can be detected. In a particularly preferred embodiment of the method, all the method steps as well as all the steps of the treatment process itself are documented in the log file, together with the time at which they were respectively performed.

Advantageously, the treatment process is interrupted, and the retort cover unlocked, only when an actuation of the second operating element is sensed within a predetermined time after display of the prompt begins. If the operator does not actuate the second operating element within that predetermined time, an interruption of the treatment process then does not occur. Inadvertent actuation of only the first operating element therefore still has no influence at all on execution of the treatment process.

A sensor preferably detects whether the retort cover is open or closed. The information acquired by the sensor regarding the closure state of the retort cover can be used to control the tissue processor, in particular during the interruption of the treatment process. For example, the tissue processor can be controlled in such a way that the retort cover is automatically locked (and the treatment process is continued) when the sensor detects, during the interruption of the treatment process, that the open retort cover has been closed again by the operator.

Alternatively, if the retort cover is closed and unlocked during the interruption of the treatment process, it is possible to lock it again, and to continue the treatment process, only by once again actuating the first operating element. In this embodiment, the first operating element therefore serves both to lock and to unlock the closed retort cover.

In a preferred refinement of the tissue processor according to the present invention, the retort cover has a grip lever that is movable into an opening position in order to open the retort cover, and into a closing position in order to close the retort cover. The mechanism intended to lock and unlock the closed retort cover is embodied in this case to block the grip lever in its closing position in order to lock the retort cover, and to release the grip lever in its closing position in order to unlock the retort cover. Locking and unlocking of the retort cover therefore occurs in this case by way of the grip lever, which simultaneously serves to open and close the retort cover manually.

The first operating element is preferably a button that is arranged on a housing of the tissue processor, and thus physically separately from the retort cover.

In a further advantageous refinement, the display apparatus of the tissue processor contains a touch screen. In this refinement, the second operating element is a graphical user interface presented on the touch screen, e.g. a key area that the operator actuates by pressing onto the touch screen.

In this case the first operating element can also be part of the user interface, e.g. a key area that can be actuated by pressing onto the touch screen.

BRIEF DESCRIPTION OF THE DRAWINGS

The invention will be explained below on the basis of an exemplifying embodiment with reference to the drawings, in which.

DETAILED DESCRIPTION OF THE DRAWINGS

Figure 1:
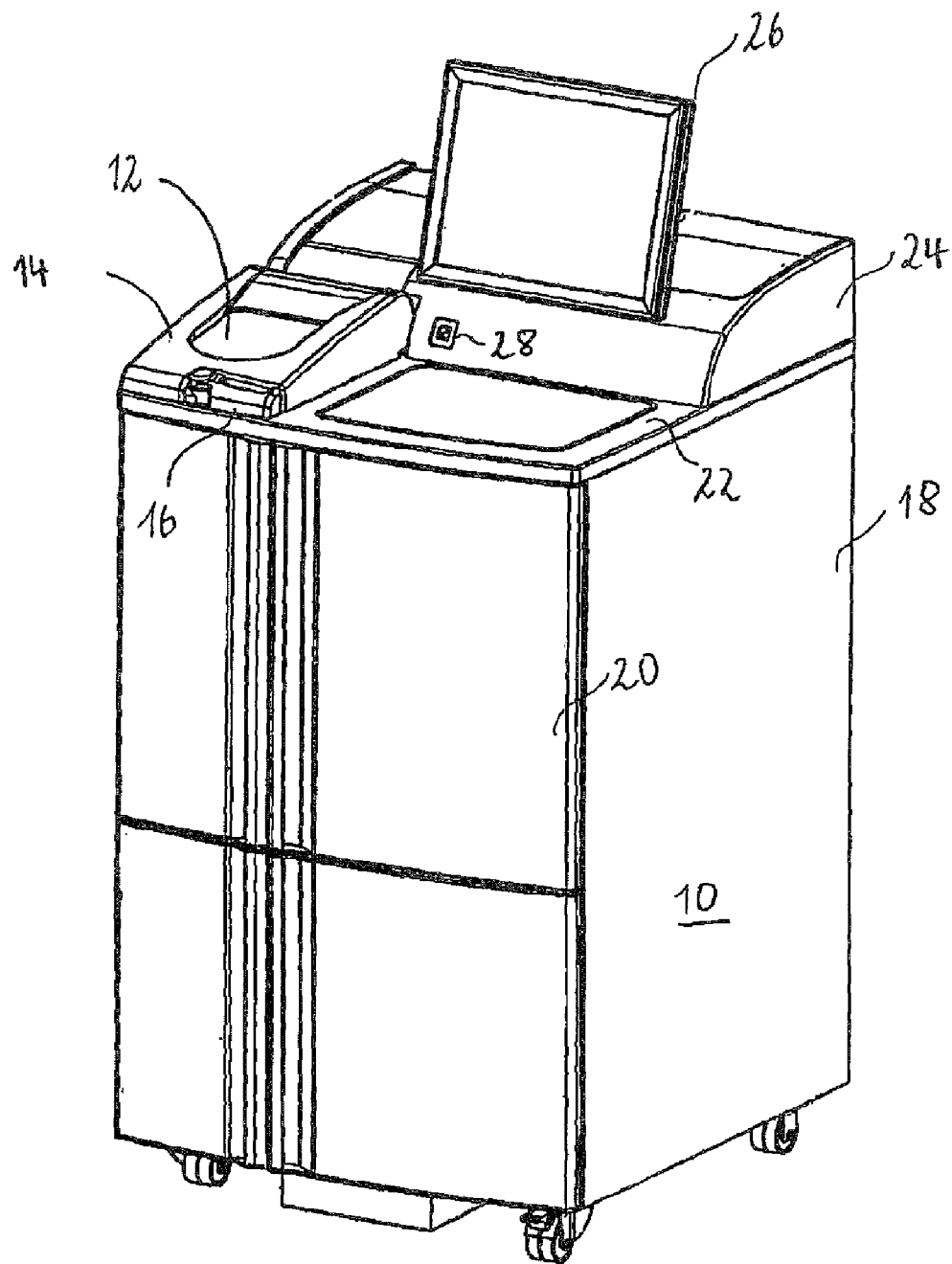
FIG. 1 is a perspective view of a tissue processor.

FIG. 1 schematically shows a tissue processor 10 with which the method according to the invention can be carried out. Tissue processor 10 contains a retort 12 in which tissue samples can be treated with various reagents. Retort 12 has a retort cover 14 having a grip lever 16 that is actuated by an operator for manual opening and closing of retort cover 14. Retort cover 14 is shown in the closed state in FIG. 1.

Tissue processor 10 encompasses a housing 18 having drawers 20. As depicted in FIG. 1, drawers 20 are slid into housing 18. The reagents are accordingly not shown in FIG. 1.

Arranged on a desktop 22 is a console 24 on which a contact-sensitive touch screen 26 is mounted. A graphical user interface having a variety of key areas, with which the operator can perform inputs in order to control tissue processor 10, can be presented on touch screen 26. Located on the front side of console 24 is a button 28 that is actuated by the operator in order to unlock and lock retort cover 14, as described in detail below.

Figure 2:
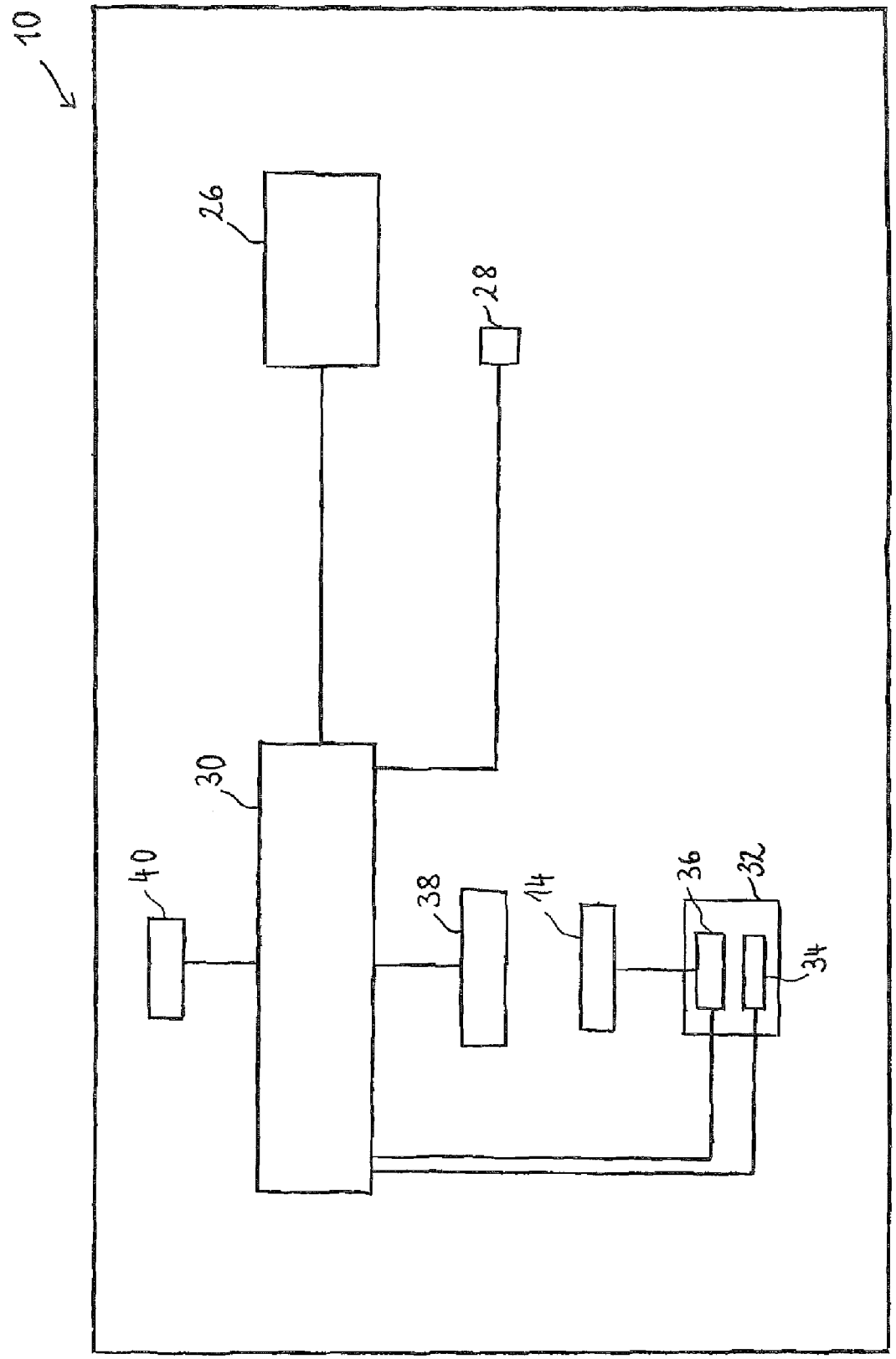
FIG. 2 is a block diagram of the tissue processor.

FIG. 2 depicts functionally important components of tissue processor 10 in a block diagram.

Tissue processor 10 contains a central processor unit (abbreviated CPU) 30, to which touch screen 26 and button 28 shown in FIG. 1 are connected. Tissue processor 10 further contains a mechanism 32 having a sensor 34 and an actuator 36, both of which are connected to CPU 30. Actuator 36 acts on grip lever 16 in order to lock and unlock it, in a manner described later, when retort cover 14 is closed.

Tissue processor 10 further contains a ventilation apparatus 38 that is in communication with retort 12 and has the function of extracting, for example toward the back side of tissue processor 10, the vapors produced in retort 12 by the reagents. Ventilation apparatus 38 comprises, for example, at least two fans that are arranged in housing 18 on the back side of retort 12 and can each be operated at at least two different rotation speeds. The higher the rotation speed, the greater the extraction power level of the respective fan at which it extracts, for example through slots that are configured in a back wall of retort 12, the vapors occurring in retort 12.

Also provided is a memory 40 that is connected to CPU 30 and serves to store a log file.

CPU 30, touch screen 26 with the user interface presented on it, button 28, mechanism 32, and memory 40 are part of a control device that controls tissue processor 10.

Figure 3:
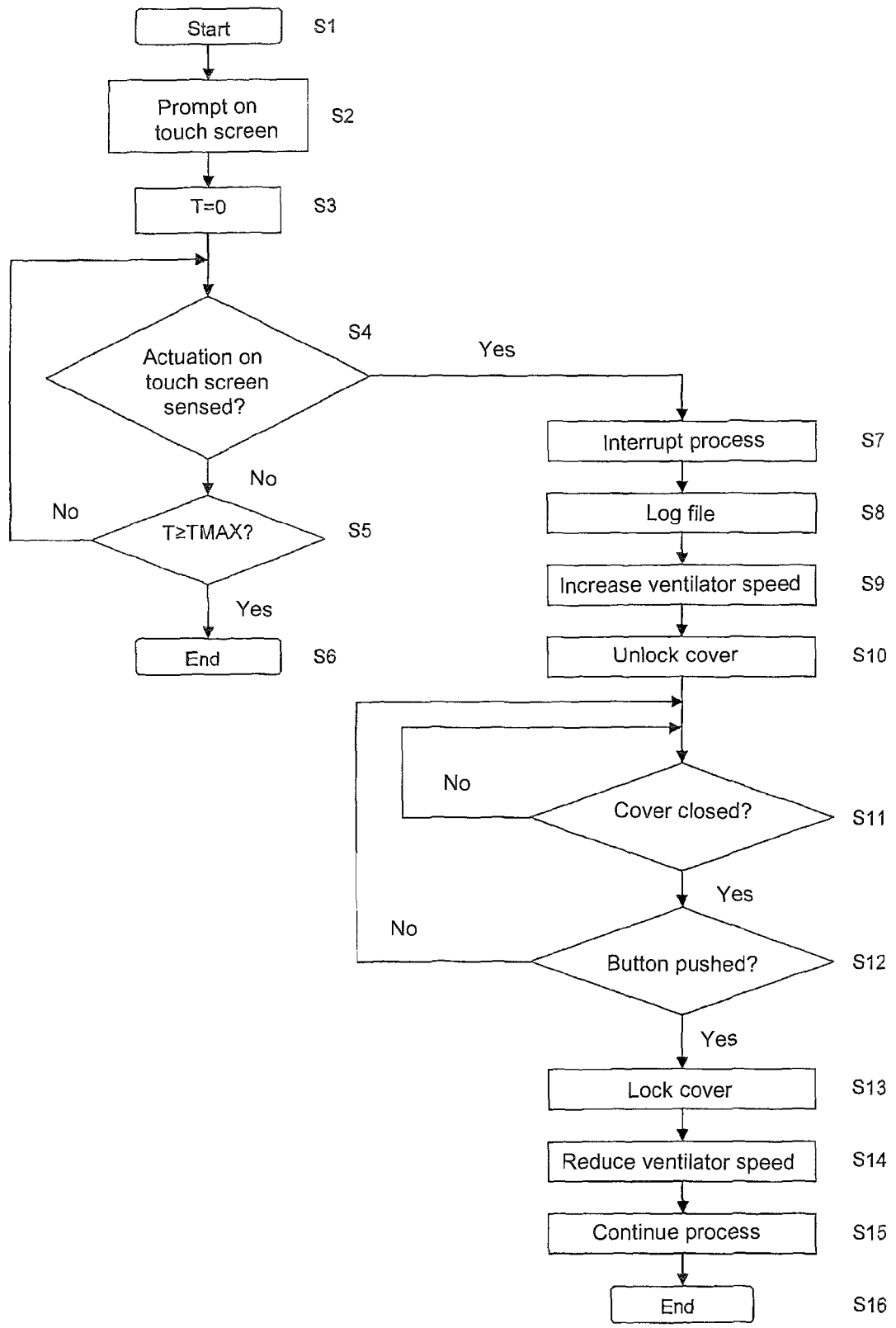
FIG. 3 is a flow chart with method steps that are carried out in the context of the method according to the present invention.

The method according to the present invention for controlling the tissue processor will be described below with reference to an exemplifying embodiment. FIG. 3 shows a flow chart that shows some of the method steps to be carried out in this exemplifying embodiment.

The operator firstly introduces into retort 12 the tissue samples that are to be treated, and then closes retort cover 14. The operator does so by bringing grip lever 16 into its closing position. Sensor 34 then senses that retort cover 14 has been closed, and outputs a corresponding signal to CPU 30.

CPU 30 then instructs actuator 36 to lock retort cover 14. Once retort cover 14 is locked, the treatment process begins.

If the operator wishes to open retort cover 14 during execution of the treatment process, he or she actuates button 28 arranged on console 24.

FIG. 3 depicts the part of the method that is initiated by pressing button 28. This part of the method therefore begins in step S1 with the actuation of button 28. CPU 30 then, in step S2, instructs touch screen 26 to display, via the graphical user interface that is presented on touch screen 26, a message to the operator. This message contains, for example, the information that a treatment process is currently being carried out. This message further contains, for example, a prompt to the operator to confirm the unlocking of retort cover 14, as requested by pressing button 28, by pressing a key area provided for that purpose on the user interface.

A timer is then initialized in step S3. In step S4, CPU 30 checks whether the key area provided on the graphical user interface for confirmation of the unlocking of retort cover 14 has or has not been pressed by the operator. If the key area has not been pressed, CPU 30 then checks (in step S5) whether the timer started in step S3 has reached a predetermined time TMAX. If not, execution returns to step S4.

Steps S4 and S5 are repeated as long as no actuation of the key surface is sensed in step S4. This continues until the timer started in step S3 reaches the predetermined time TMAX. In that case the part of the method shown in FIG. 3 ends with step S6, meaning that the treatment process continues to be executed with no interruption.

If it is found in step S4, however, that the key area displayed on touch screen 26 has been actuated, control execution then continues with step S7. In step S7, CPU 30 interrupts the treatment process. The CPU then, in step S8, records in the log file stored in memory 40 an information item which indicates that the treatment process has been interrupted.

In step S9, CPU 30 applies control to ventilation apparatus 38 in such a way that its fans are each operated at a higher rotation speed and thus at a higher extraction power level. In step S10, CPU 30 outputs a confirmation signal to actuator 36, instructing it to unlock retort cover 14.

In step S11, CPU 30 checks whether or not retort cover 14 is closed. CPU 30 recognizes this from the signal that is acquired by sensor 34 and outputted to CPU 30. The query in step S11 is repeated as long as retort cover 14 is not closed.

If CPU 30 determines that retort cover 14 is closed, it then checks in step S12 whether button 28 has been pressed again. If not, control execution returns to the query in step S1.

Be it noted at this juncture that the functionality of button 28 can of course also be implemented by way of the graphical user interface, for example by way of a corresponding key area that is actuated by pressing on the touch screen.

If it is ascertained in step S12 that the operator has pressed button 28 again, CPU 30 then (in step S13) outputs a command to actuator 36 instructing it to lock retort cover 14 again. CPU 30 then, in step S14, applies control to ventilation apparatus 38 so that its fans once again each operate at a slower rotation speed and thus a lower extraction power level.

In step S15, CPU 30 gives instructions for the treatment process to be continued at the point at which it was interrupted in step S7. This part of the method ends at step S17.

The execution sequence depicted in FIG. 3 is to be understood as merely an example. Individual method steps such as, for example, the sequence of steps S7 to S10 can, for example, be modified. The query loop in steps S4 to S5 can also be replaced by the fact that in addition to the key area that is provided in the user interface and is to be pressed to confirm the unlocking of retort cover 14, a further key area is displayed which must be actuated if unlocking of retort cover 14 is not desired. The entry in the log file that is stored in memory 40 can moreover also be made at a different point and, in particular, using different or additional information items.

After the part of the method depicted in FIG. 3 has been executed, the tissue samples arranged in retort 12 continue to be treated until the treatment process is complete. Once the treatment process is complete, CPU 30 outputs a command to actuator 36 instructing it to unlock retort cover 14 again. The operator can then open the unlocked retort cover 14 and remove the treated tissue samples.

Figure 4:
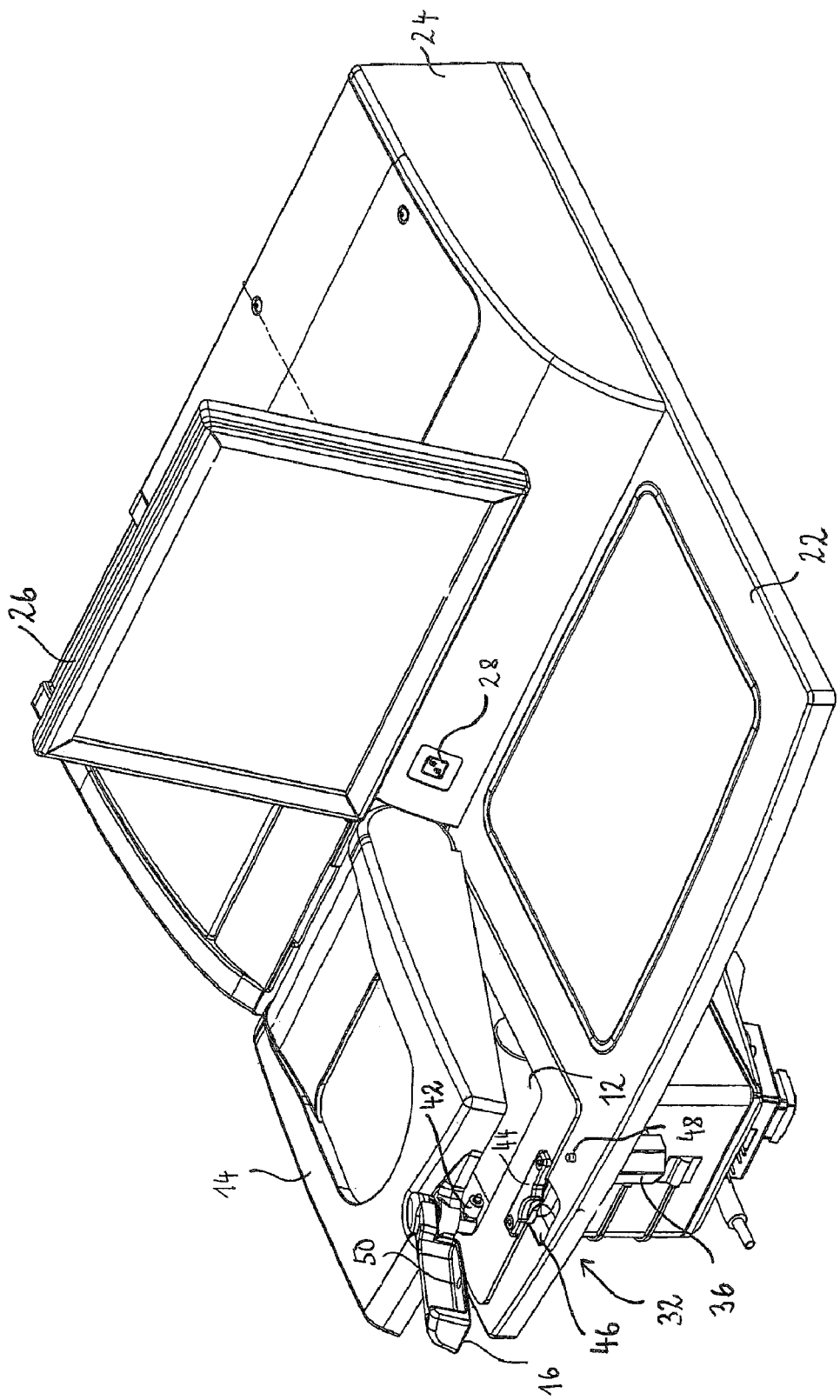
FIG. 4 is an enlarged depiction of part of the tissue processor shown in FIG. 1.

FIG. 4 is an enlarged depiction of the upper part of tissue processor 10 shown in FIG. 1, with retort cover 14 open. FIG. 4 serves to explain to coaction between the pivotable grip lever 16 and mechanism 32, depicted merely schematically in FIG. 2, in order to lock and unlock retort cover 14.

In FIG. 4, grip lever 16 is in its open position. Grip lever 16 is pivotable in a plane that is defined substantially by retort cover 14. It has, in the region of its end articulated on retort cover 14, a closure element 42 that is rotated along as the free end of grip lever 16 is pivoted.

Mechanism 32 contains a closure plate 44 that is bolted onto desktop 22 close to retort 12. A cutout 46 is present in desktop 22 beneath closure plate 44.

In order to close retort cover 14, the operator grasps grip lever 16 with his or her hand and pushes it down until closure element 42 is located in cutout 46. When grip lever 16 is then pivoted to the right (in the depiction according to FIG. 4), closure element 42 travels underneath closure plate 44 and latches into place there. Retort cover 14 is now manually closed.

In the present exemplifying embodiment, actuator 36 (depicted merely schematically in FIG. 2) of mechanism 32 is embodied as a reciprocating magnet. Reciprocating magnet 36 sits beneath desktop 22 in the vicinity of retort 12. Mounted on reciprocating magnet 36 is a stud 48 that sits in an orifice configured in desktop 22. Stud 48 serves to lock grip lever 16 when retort cover 14 is closed, by traveling into a stud hole 50.

When retort cover 14 is closed, grip lever 16 is arranged on or above desktop 22 in such a way that its stud hole 50 is aligned with the orifice, present in desktop 22, in which stud 48 displaceably sits. In order to lock the closed retort cover 14, CPU 30 instructs reciprocating magnet 36 to be energized, with the result that it moves upward (in the depiction according to FIG. 4). As a result, stud 48 mounted on reciprocating magnet 36 engages into stud hole 50. In order to unlock the retort cover, reciprocating magnet 36 is switched to the currentless state with the result that it moves back downward (in the depiction according to FIG. 4). Stud 48 mounted on reciprocating magnet 36 consequently also releases out of stud hole 50.

Sensor 36 (not shown in FIG. 4) that is provided in mechanism 32 is embodied, for example, as a microswitch.

LIST OF COMPONENT PARTS

10 Tissue processor
12 Retort
14 Retort cover
16 Grip lever
18 Housing
20 Drawer
22 Desktop
24 Console
26 Touch screen
28 Button
30 CPU
32 Mechanism 34 Sensor
36 Actuator
38 Ventilator apparatus
40 Memory
42 Closure element
44 Closure plate
46 Cutout
48 Stud
50 Stud hole
S1-S16 Method steps

What is claimed is:

1. A method for controlling a tissue processor comprising a retort for processing tissue samples therein, said retort comprising a retort cover that can be opened and closed by an operator, the method comprising the method steps of:
    locking the closed retort cover prior to tissue processing to prevent opening;
    determining the actuation state of a first operating element that can be actuated by the operator;
    prompting the operator when an actuation of the first operating element during tissue processing is determined by displaying to the operator on a display device the prompt to confirm unlocking of the closed retort cover by actuating a second operating element that can be actuated by the operator;
    determining the actuation state of the second operating element;
    interrupting tissue processing when an actuation of the second operating element is determined and the closed retort cover is unlocked;
    continuing tissue processing after the retort cover is once again locked; and
    unlocking the retort cover after having completed tissue processing.

2. The method according to claim 1, further comprising the method steps of:
    connecting a ventilator apparatus to the retort;
    operating said ventilator apparatus at a first power level during tissue processing; and
    operating said ventilator apparatus at a second power level that is higher than the first power level during the interruption of tissue processing.

3. The method according to claim 1, further comprising the method step of recording at least one of the method steps in a log file.

4. The method according to claim 3, wherein the recorded method step is interrupting tissue processing.

5. The method according to claim 1, further comprising the method steps of measuring the time from the point in time the prompt was first displayed, and enabling interrupting of tissue processing and unlocking the retort cover only when actuation of the second operating element is determined within a predetermined maximum time that has been measured.

6. The method according to claim 1, further comprising the method step of determining by means of a sensor whether the retort cover is open or closed.

7. The method according to claim 6, further comprising the method step of locking the retort cover again and continuing tissue processing by actuating the first operating element if during a tissue processing interruption it is determined that the retort cover is closed and unlocked.

8. A tissue processor for processing tissue samples, comprising:
    a control device for controlling the tissue processor, comprising
        a mechanism for locking and unlocking a closed retort cover,
        a first operating element that can be actuated by an operator,
        a second operating element that can be actuated by the operator, and
        a display apparatus; and
    a retort in that the tissue is processed and that is connected to the retort cover to be opened and closed by an operator;
    wherein the control device is adapted to:
        lock the closed retort cover by means of the mechanism to prevent opening prior to starting tissue processing;
        determine an actuation state of the first operating element;
        instruct the display apparatus to display a prompt to the operator to confirm the unlocking of the closed retort cover by actuating the second operating element when an actuation of the first operating element during tissue processing is determined;
        determine an actuation state of the second operating element;
        interrupt the treatment process and unlock the closed retort cover by means of the mechanism when an actuation of the second operating element is determined;
        continue the treatment process after the retort cover is once again locked; and
        unlock the retort cover by means of the mechanism after tissue processing is complete.

9. The tissue processor according to claim 8, comprising a ventilator apparatus connected to the retort, said ventilator apparatus being controlled by the control device so that the ventilator apparatus is operated at a first power level during tissue processing, and at a second power level that is higher than the first power level during the interruption of the treatment process.

10. The tissue processor according to claim 8, wherein the control device has a memory for storing a log file recording at least one operation carried out by the control device.

11. The tissue processor according to claim 10, wherein the at least one recorded operation is the interruption of tissue processing.

12. The tissue processor according to claim 8, wherein the mechanism contains a sensor for sensing the closure state of the retort cover.

13. The tissue processor according to claim 8, wherein
    the retort cover has a grip lever that is movable into an opening position in order to open the retort cover, and into a closing position in order to close the retort cover; and
    the mechanism is embodied to block the grip lever in its closing position in order to lock the retort cover, and to release the grip lever in its closing position in order to unlock the retort cover.

14. The tissue processor according to claim 13, wherein
    the mechanism contains a movable reciprocating magnet that is energized by the control device in order to lock the closed retort cover, and is disconnected from electrical power in order to unlock the closed retort cover, the reciprocating magnet being arranged in a first position when energized and in a second position when disconnected from electrical power;
    a stud mounted on the reciprocating magnet is arranged in a stud hole configured in the grip lever, and blocks the grip lever, when the reciprocating magnet is in the first position and the retort cover is closed; and the stud is removed from the stud hole, and releases the grip lever, when the reciprocating magnet is in the second position and the retort cover is closed.

15. The tissue processor according to claim 8, wherein the first operating element is a button arranged on a housing of the tissue processor.

16. The tissue processor according to claim 8, wherein the display apparatus contains a touch screen, and the second operating element is a key area of a graphical user interface presented on the touch screen.

* * * * *